(12) United States Patent
Zerhusen et al.

(10) Patent No.: US 12,144,608 B2
(45) Date of Patent: Nov. 19, 2024

(54) THREE-MODE PATIENT CHAIR EXIT SENSING

(71) Applicant: Hill-Rom Services, Inc., Batesville, IN (US)

(72) Inventors: Robert M. Zerhusen, Batesville, IN (US); Tyler Holmes, Batesville, IN (US); Nicholas A. Mann, Cincinnati, OH (US); Ibne Soreefan, Batesville, IN (US)

(73) Assignee: Hill-Rom Services, Inc., Batesville, IN (US)

(*) Notice: Subject to any disclaimer, the term of this patent is extended or adjusted under 35 U.S.C. 154(b) by 282 days.

(21) Appl. No.: 17/832,779

(22) Filed: Jun. 6, 2022

(65) Prior Publication Data
US 2022/0400979 A1 Dec. 22, 2022

Related U.S. Application Data

(60) Provisional application No. 63/213,318, filed on Jun. 22, 2021.

(51) Int. Cl.
| | |
|---|---|
| *A61B 5/11* | (2006.01) |
| *A61B 5/00* | (2006.01) |
| *A61B 5/01* | (2006.01) |
| *A61G 7/05* | (2006.01) |
| *A61M 5/14* | (2006.01) |

(52) U.S. Cl.
CPC .......... *A61B 5/1115* (2013.01); *A61B 5/0075* (2013.01); *A61B 5/01* (2013.01); *A61B 5/1117* (2013.01); *A61B 5/1126* (2013.01); *A61B 5/7282* (2013.01); *A61B 5/746* (2013.01); *A61G 7/0524* (2016.11); *A61M 5/1415* (2013.01)

(58) Field of Classification Search
CPC ...... A61B 5/1115; A61B 5/1117; A61B 5/746
See application file for complete search history.

(56) References Cited

U.S. PATENT DOCUMENTS

| | | |
|---|---|---|
| 5,276,432 A | 1/1994 | Travis |
| 6,208,250 B1 | 3/2001 | Dixon et al. |
| 6,791,460 B2 | 9/2004 | Dixon et al. |
| 7,985,953 B2 | 7/2011 | Luterotti et al. |
| 7,987,069 B2 | 7/2011 | Rodgers et al. |
| 8,514,280 B2 | 8/2013 | Zisa et al. |
| 9,974,612 B2 | 5/2018 | Pinter et al. |
| 10,198,813 B2 | 2/2019 | Hata et al. |
| 10,231,647 B2 | 3/2019 | Kostic et al. |
| 10,568,547 B1 | 2/2020 | Johanning |
| 10,674,941 B2 | 6/2020 | Tanaka et al. |

(Continued)

FOREIGN PATENT DOCUMENTS

GB 2581767 A 9/2020

*Primary Examiner* — Joel Lamprecht
*Assistant Examiner* — Nyrobi Celestine
(74) *Attorney, Agent, or Firm* — Barnes & Thornburg LLP

(57) ABSTRACT

A system for contactless monitoring of a person in a chair includes a detector mount positioned adjacent the chair and detached from the chair. A detector is coupled to the detector mount and is configured to detect thermal radiation from a field of view that includes the chair. A controller controls the detector. The controller includes a processor and a nontransitory memory device that includes instructions that are performed by the processor to control the detector.

20 Claims, 11 Drawing Sheets

(56) References Cited

U.S. PATENT DOCUMENTS

| | | |
|---|---|---|
| 10,694,956 B2 | 6/2020 | Dumoulin et al. |
| 10,786,408 B2 | 9/2020 | Sidhu et al. |
| 10,806,377 B2 | 10/2020 | Kilcran et al. |
| 10,904,492 B2 | 1/2021 | Derenne et al. |
| 2010/0245090 A1* | 9/2010 | Smith .................. H10N 10/854 340/573.1 |
| 2011/0241886 A1 | 10/2011 | Receveur |
| 2013/0267791 A1* | 10/2013 | Halperin .............. A61B 5/6891 600/300 |
| 2015/0112151 A1 | 4/2015 | Muhsin et al. |
| 2016/0015277 A1* | 1/2016 | Dumoulin .......... G08B 21/0208 600/301 |
| 2016/0307429 A1* | 10/2016 | Hood .................. G08B 3/1016 |
| 2017/0119285 A1* | 5/2017 | Fu ........................ A61B 5/1127 |
| 2017/0150905 A1* | 6/2017 | Shen .................. G08B 21/0453 |
| 2019/0046364 A1* | 2/2019 | Kilcran ................ A61B 5/0022 |
| 2019/0110763 A1* | 4/2019 | Brasch .................. A61B 5/1115 |
| 2019/0231231 A1 | 8/2019 | Saria et al. |
| 2020/0051251 A1* | 2/2020 | Chronis ..................... G06T 7/11 |
| 2020/0060910 A1* | 2/2020 | Lightcap ............. A61B 5/1128 |
| 2020/0221977 A1* | 7/2020 | Tanaka ................. G08B 21/043 |
| 2021/0076946 A1* | 3/2021 | Spickermann ......... A61B 5/015 |

* cited by examiner

THREE-MODE PATIENT CHAIR EXIT SENSING

CROSS-REFERENCE TO RELATED APPLICATIONS

This application claims priority under 35 U.S.C. § 119(e) to U.S. Provisional Application No. 63/213,318, filed Jun. 22, 2021, which is expressly incorporated by reference herein.

BACKGROUND

The present disclosure relates to patient support apparatuses and, more particularly, to a system for contactless monitoring of a person in a chair.

Generally, patient falls are a chronic problem for health care facility. Although most patients are a fall risk and bed exit systems are utilized to monitor a patient's movement in a bed, patients are not always protected or monitored while in a chair of the health care facility. Some health care facilities utilize pads that the patient sits on while in a chair. However, these pads can be unreliable and are not widely used by most staff in the health care facility. Many patients are unwilling or unable to lay in the hospital bed for an extended period of time. For example, med-surge patient data shows that patients may spend up to 40% to 50% of their time in a patient chair. Accordingly, there is a lack in alternatives to safely monitor these patients.

SUMMARY

The present disclosure includes one or more of the features recited in the appended claims and/or the following features which, alone or in any combination, may comprise patentable subject matter.

According to a first aspect of the disclosed embodiments, a system for contactless monitoring of a person in a chair includes a detector mount positioned adjacent the chair and detached from the chair. A detector is coupled to the detector mount and is configured to detect thermal radiation from a field of view that includes the chair. A controller controls the detector. The controller includes a processor and a nontransitory memory device that includes instructions that are performed by the processor to control the detector. The controller processes data related to the thermal radiation from the field of view and detected by the detector to determine a status of the person from one of at least three statuses.

In some embodiments of the first aspect, the one of at least three statuses may include positioned in the chair, exiting the chair, and out of the chair. An alert system may be configured to alert the person to return to the position in the chair when the person is determined to be exiting the chair. The controller may determine a fourth status of the person by processing the data related to the thermal radiation from the field of view. The fourth status may be that the person is moving between the chair and a patient support apparatus. The controller may determine a fifth status of the person by processing the data related to the thermal radiation from the field of view. The fifth status may indicate that the person is falling based on a rate of change of the position of the person.

It may be desired, in the first aspect, that the field of view includes a 65 degree cone scanning field. The controller may determine a temperature of the person by processing the data related to the thermal radiation from the field of view. The controller may alert a caregiver if the temperature of the person exceeds a predetermined value. The controller may identify pressure sores on the person based on the detected temperature of the person.

It may be contemplated, in the first aspect, that the detector includes a thermal camera. The thermal camera may include a forward-looking infrared camera. A remote display device may display a thermal image from the field of view. The remote display device may be a mobile device carried by a caregiver.

According to a second aspect of the disclosed embodiments, a system for contactless monitoring of a person includes a first patient support apparatus. A second patient support apparatus is positioned adjacent to and detached from the first patient support apparatus. A detector is coupled to the first patient support apparatus and is configured to detect thermal radiation from a field of view detected by the detector and including the second patient support apparatus. A controller controls the detector. The controller includes a processor and a nontransitory memory device that includes instructions that are performed by the processor to control the detector. The controller processes data related to the thermal radiation from the field of view to determine a status of a person at the second patient support apparatus from one of at least three statuses.

Optionally, in the second aspect, the first patient support apparatus may include a bed and the second patient support apparatus may include a chair. The detector may be coupled to a siderail of the first patient support apparatus. The detector may be coupled to an intravenous pole of the first patient support apparatus.

In some embodiments of the second aspect, the one of at least three statuses may include positioned in the second patient support apparatus, exiting the second patient support apparatus, and out of the second patient support apparatus. The controller may determine a fourth status of the person by processing the data related to the thermal radiation from the field of view. The fourth status may be that the person is moving between the second patient support apparatus and the first patient support apparatus. The controller may determine a fifth status of the person by processing the data related to the thermal radiation from the field of view. The fifth status may indicate that the person is falling based on a rate of change of the position of the person.

It may be desired, in the second aspect, that the field of view includes a 65 degree cone scanning field. The controller may determine a temperature of the person by processing the data related to the thermal radiation from the field of view. The detector may include a thermal camera. A remote display device may display a thermal image from the field of view.

According to a third aspect of the disclosed embodiments, a method for contactless monitoring of a person, includes detecting, with a detector coupled to a first patient support apparatus, thermal radiation from a field of view including a second patient support apparatus. The method also includes processing data related to the thermal radiation from the field of view to determine a status of a person within the field of view from one of at least three statuses. The one of at least three statuses includes positioned in the second patient support apparatus, exiting the second patient support apparatus, and out of the second patient support apparatus.

In some embodiments of the third aspect, the method may also include determining a fourth status of the person by processing the data related to the thermal radiation from the field of view. The fourth status may be that the person is moving between the second patient support apparatus and the first patient support apparatus. The method may also include determining a fifth status of the person by processing the data related to thermal radiation from the field of view. The fifth status may indicate that the person is falling based on a rate of change of the position of the person. The method may also include alerting the person to return to the position in the second patient support apparatus when the person is determined to be exiting the second patient support apparatus.

Optionally, in the third aspect, the method may also include detecting thermal radiation from a field of view includes detecting thermal radiation within a 65 degree cone scanning field. The method may also include determining a temperature of the person by processing the data related to the thermal radiation from the field of view. The method may also include displaying a thermal image from the field of view on a remote display device.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
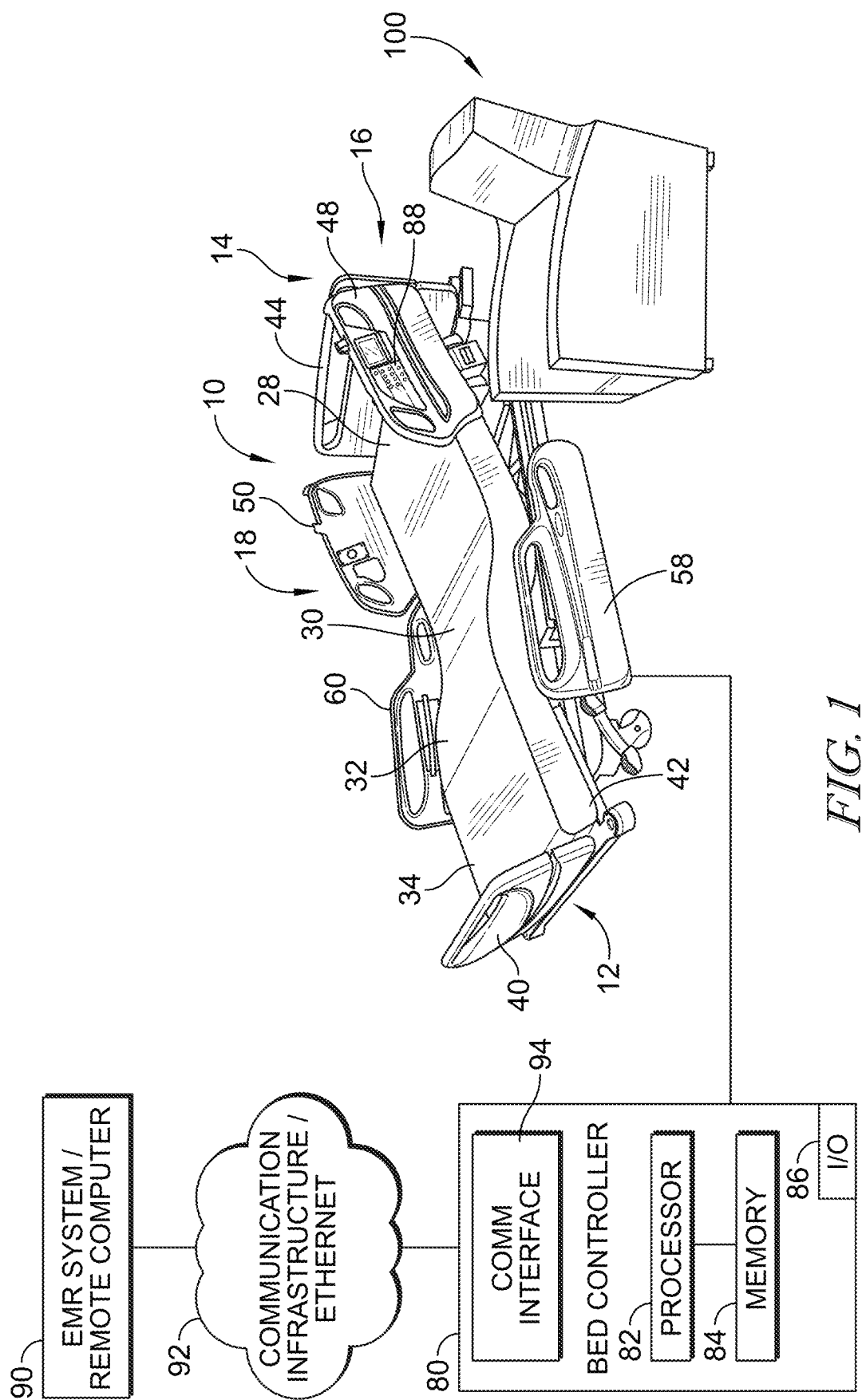
FIG. 1 is schematic view of a healthcare facility having a patient chair positioned adjacent a patient bed, wherein the patient bed is in communication with a network of the healthcare facility.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a patient support apparatus 10 is illustratively embodied as a hospital bed 10. For purposes of orientation, the discussion of the hospital bed 10 will be based on the orientation of a patient supported on the hospital bed 10 in a supine position. Thus, the foot end 12 of the hospital bed 10 refers to the end nearest the patient's feet when the patient is supported on the hospital bed 10 in the supine position. The hospital bed 10 has a head end 14 opposite the foot end 12. A left side 16 refers to the patient's left when the patient is lying in the hospital bed 10 in a supine position. The right side 18 refers to the patient's right. A longitudinal length of the hospital bed 10 extends between the head end 14 and foot end 12 of the hospital bed 10. Similarly, a lateral width of the hospital bed 10 extends between the left side 16 and right side 18.

The bed 10 includes a head section 28, a seat section 30, thigh section 32, and a foot section 34. A foot panel 40 is supported from the foot section 34 and extends vertically from an upper surface 42 to form a barrier at the foot end 12 of the hospital bed 10. A head panel 44 extends vertically to form a barrier at the head end 14 of the hospital bed 10. A left head siderail 48 is supported from the head section 28 and is moveable between a raised position shown in FIG. 1 and a lowered position as is known in the art. A right head siderail 50 is also moveable between the raised position of FIG. 1 and lowered position. The hospital bed 10 also includes a left foot siderail 58 and a right foot siderail 60. Each of the siderails 48, 50, 58, and 60 are operable to be lowered to a position below the upper surface 42. It should be noted that when the head section 28 is moved, the head siderails 48 and 50 move with the head section 28 so that they maintain their relative position to the patient. This is because both of the head siderails 48 and 50 are supported by the head section 28.

The bed 10 includes a controller 80 that may be positioned in the foot panel 40 or the head panel 44 of the bed 10. In some embodiments, the controller 80 may be positioned within one of the siderails 48, 50, 58, or 60. The controller 80 includes a micro-processor 82, a memory 84, and an input/output (I/O) 86 connected to a graphical user interface (GUI) 88. The controller 80 enables a user to operate various features of the bed 10 via the GUI 88. In the illustrative embodiment, the GUI 88 is positioned on the left head siderail 48; however, in some embodiments the GUI 88 may be positioned on any of siderails 50, 58, or 60. The GUI 88 may also be positioned on the foot panel 40 of the bed 10. Some embodiments of bed 10 may include multiple GUIs 88, e.g. one GUI 88 on the left head siderail 48 and one GUI 88 on the right head siderail 50.

The controller 80 of the bed 10 may communicate with the remote devices 90, e.g. remote computers, via communication infrastructure 92 such as an Ethernet of a healthcare facility in which bed 10 is located and via communications links. The remote devices 90 may be part of an electronic medical records (EMR) system. However, the controller 80 of the bed 10 may communicate with other computers such as those included as part of a nurse call system, a physician ordering system, an admission/discharge/transfer (ADT) system, or some other system used in a healthcare facility in other embodiments. In the illustrative embodiment, bed 10 has a communication interface or port 94 which provides bidirectional communication with remote devices 90.

Another patient support apparatus 100 is illustratively embodied as a chair 100. The chair 100 is positioned in a healthcare facility room adjacent the bed 10. In the illustrative embodiment, the chair 100 is positioned on the left side 16 of the bed 10. It will be appreciated that the chair 100 may also be positioned on the right side 18 of the bed 10. When the patient is occupying the healthcare facility room, the patient is generally positioned in one of the bed 10 or the chair 100. Over time, the patient may move between the bed 100 and the chair 10. The disclosed embodiments describe a system and method for monitoring the patient's position relative to the chair. In particular, the position of the patient is monitored in one or more of a plurality of modes. In a first mode, the patient is detected as being positioned within the chair 100. In an second mode, the patient is detected as exiting the chair 100. In a third mode, the patient is detected as being out of the chair 100. In a fourth mode, the patient is detected as moving between the chair 100 and the bed 10. In a fifth mode, the patient may be detected as being a fall risk.

Figure 2:
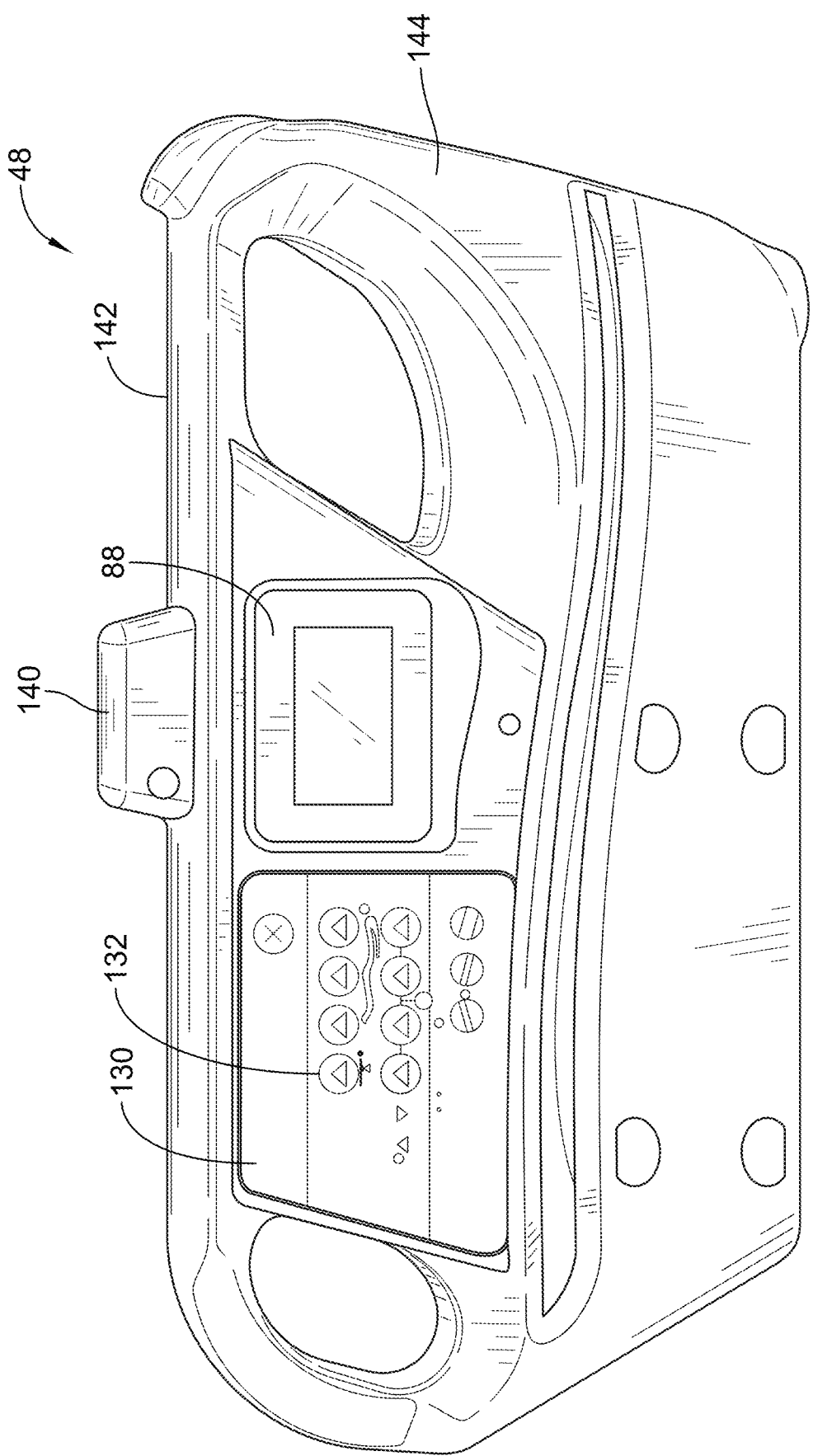
FIG. 2 is a side elevation view of a side rail of the patient bed including a patient position monitoring (PPM) system for contactless monitoring of a person in the patient chair.

Referring now to FIG. 2, the left head siderail 48 is illustrated as including a patient position monitoring (PPM) system 120 (shown in detail in FIGS. 3 and 4) for contactless monitoring of the patient on the left side 16 of the bed 10. In some embodiments, the PPM system 120 may be provided on the right head siderail 50 for contactless monitoring of the patient on the right side 18 of the bed 10. It will be appreciated that the bed may include a PPM system 120 on both the left head siderail 48 and the right head siderail 50 to provide flexibility in positioning the chair 100 in the healthcare facility room. In at least one embodiment, at least a portion of the PPM system 120 is coupled to an intravenous pole connected to the bed 10 (as described in more detail below).

A user inputs panel 130 and the GUI 88 are provided on the left head siderail 48 in the illustrative embodiment. The panel 130 includes various buttons 132 that are used by a caregiver (not shown) to control associated functions of the bed 10. For example, the panel 130 includes buttons that are used to operate various motors (not shown) to move various sections of the bed 10 as is known in the art. The panel 130 also includes buttons that are used to operate the PPM system 120. In some embodiments, the buttons of panel 130 include membrane switches. In some embodiments, the buttons of the panel 130 include touch-screen icons. The controller 80 receives user input commands from the GUI 88 and the panel 130.

The PPM system 120 includes a detector 140 positioned in the siderail 48. In the illustrative embodiment, the detector 140 is positioned at a top 142 of the siderail 48; however, in some embodiments, the detector 140 may be positioned with a body 144 of the siderail 48. In one embodiment, the detector 140 is positioned on an intravenous pole (not shown) that is coupled to the bed 10. The detector 140 is a thermal camera that creates a thermal image using infrared radiation within wavelengths from approximately 1,000 nm to approximately 14,000 nm. The thermal image displays a level of heat detected by the camera (as described in more detail below). In some embodiments, the detector 140 is a Forward-looking infrared (FLIR) camera that senses infrared radiation to detect warm objects against a cooler background. In some embodiments, the detector 140 may incorporate a stereo camera in addition to a thermal camera.

Figure 3:
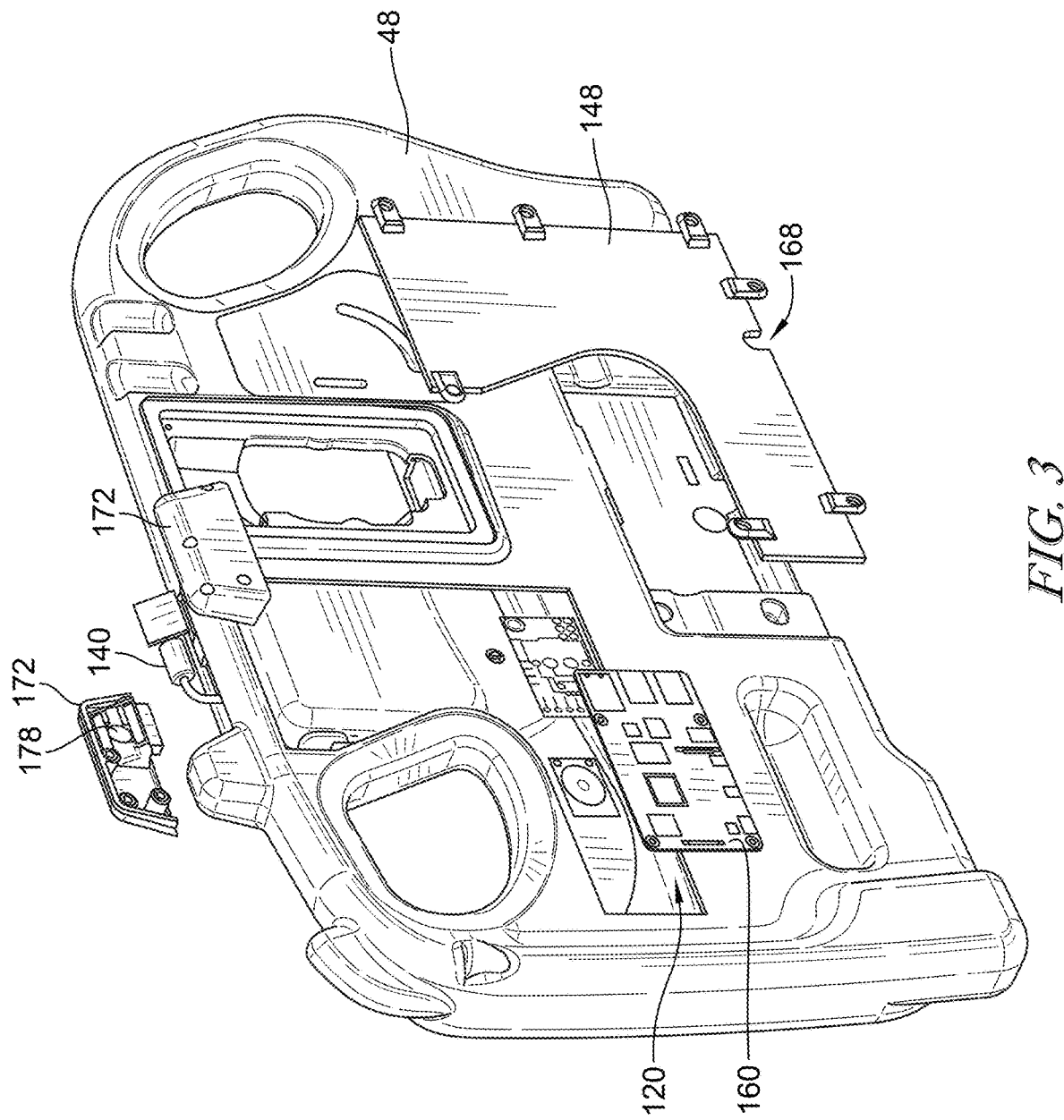
FIG. 3 is an exploded view of the side rail shown in FIG. 2 and illustrating the components of the PPM system for contactless monitoring.
Figure 4:
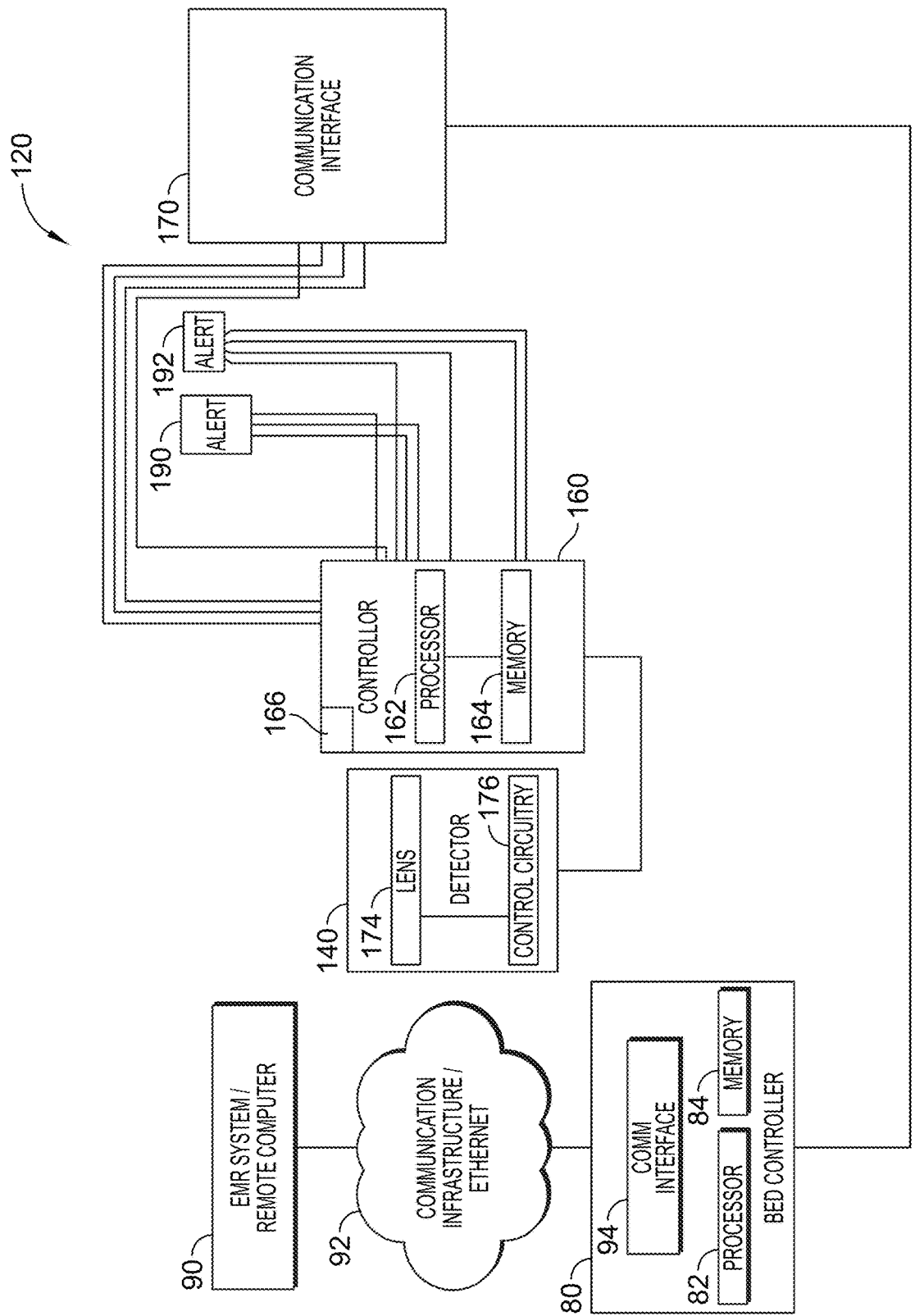
FIG. 4 is a schematic view of the PPM system for contactless monitoring, wherein the PPM system includes a detector for detecting thermal radiation within a field of view.

Referring now to FIGS. 3 and 4, a panel 148 of the siderail 48 is illustrated as being removed to show the entire PPM system 120 that is positioned within the siderail 48, as shown in FIG. 3. The PPM system 120 includes a controller 160 that is positioned behind the panel 148. The controller 160 is illustrated in FIG. 4 as having a micro-processor 162 and a memory 164 that includes instructions for controlling the processor 162. The controller 160 includes a power port 166 to receive a power cord (not shown) that extends through an opening 168 in the panel 148. The opening 168 may also be configured to receive a cable, e.g. a universal serial bus cable, to directly connect a device to the controller 160. The controller 160 enables a user to operate various features of the PPM system 120 via the GUI 88 and the user inputs panel 130. The controller 160 is connected to a communication module 170 that enables communication with the controller 80 so that the GUI 88 and the user inputs panel 130 may be used to operate the controller 160. The communication module 170 enables wireless communication between the controller 160 and the controller 80. Through the communication module 170, the controller 160 is capable of communicating with the remote devices 90 within the healthcare facility. As illustrated in FIG. 3, the communications module 170 is also positioned behind the panel 148.

The detector 140 is positioned within a pair of panels 172 at the top 142 of siderail 48 so that the detector 140 is housed within the panels 172, as shown in FIG. 3. Referring to FIG. 4, the detector 140 includes a lens 174 and control circuitry 176 that is configured to operate the lens 174. The lens 174 extends through an opening 178 in one of the panels 172. The memory 164 of the controller 160 includes instructions for operating the processor 162 to control the detector 140 so that the detector 140 operates in at least one of the modes described above and described in more detail below.

Still referring to FIGS. 3 and 4, an alert 190 embodied as a speaker and an alert 192 embodied as a light, e.g. a light emitting diode, are coupled to the controller 160. The alerts 190 and 192 are configured to provide a warning to the patient or a caregiver when the detector 140 detects a particular movement of the patient, as defined by a selected operating mode. The communication module 170 also enables the controller 160 to operate various features of the bed 10. Accordingly, alerts provided on the bed, e.g. speakers and lights, may also be activated when the detector 140 detects a particular movement of the patient.

Because the communications module 170 enables communication between the controller 160 and the controller 80, the PPM system 120 is configured to transmit the thermal image detected by the detector to the remote computers 90. As such, the thermal image is available at multiple locations throughout the healthcare facility, e.g. on a handheld device of a caregiver. Additionally, alerts from the PPM system 120 that the detector has detected a particular movement of the patient may be sent to the remote devices 90, as described in more detail below.

Figure 5:
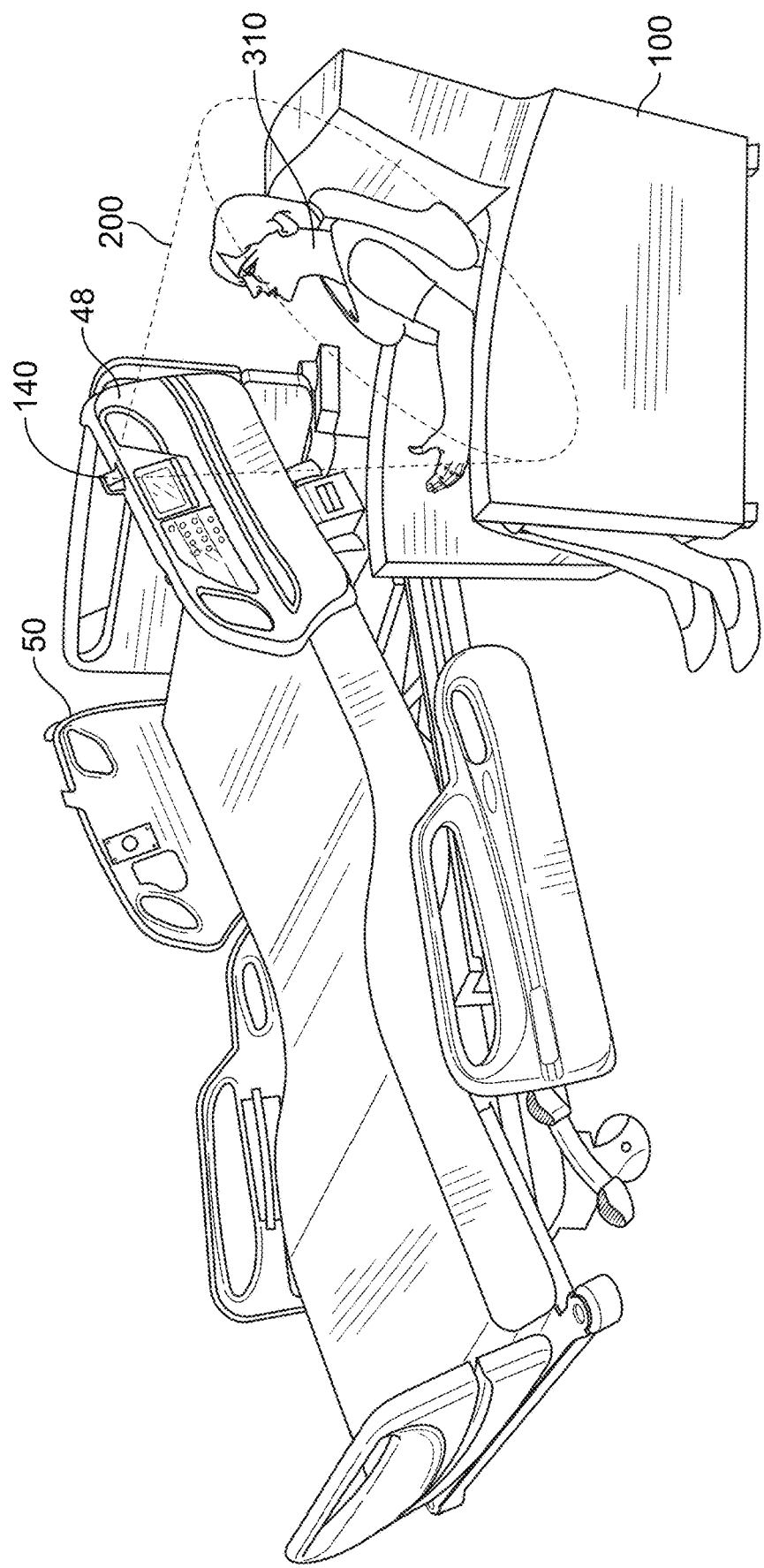
FIG. 5 is a perspective view of the field of view of the detector shown in FIG. 4.

Referring now to FIG. 5, the detector 140 detects thermal radiation within a field of view 200. The field of view 200 extends from the left head siderail 48 of the bed 10. It will be appreciated that when the detector 140 is coupled to the right head siderail 50, the field of view 200 extends from the right head siderail 50. The field of view 200 extends at a cone angle in the illustrative embodiment. In other embodiments, the field of view 200 may extend in other geometrical patterns. In one embodiment, the field of view 200 extends at an approximately 65 degree cone angle. In some embodiments, the field of view may extend at a cone angle within a range of 30 degrees to 90 degrees. In some embodiments, the field of view 200 extends at a 180 degree cone angle. The chair 100 is positioned within the field of view 200. Accordingly, the detector 140 detects thermal radiation from the chair 100. When a patient 310 is positioned within the chair 100, the field of view 200 detects thermal radiation from the patient 310.

Figure 6:
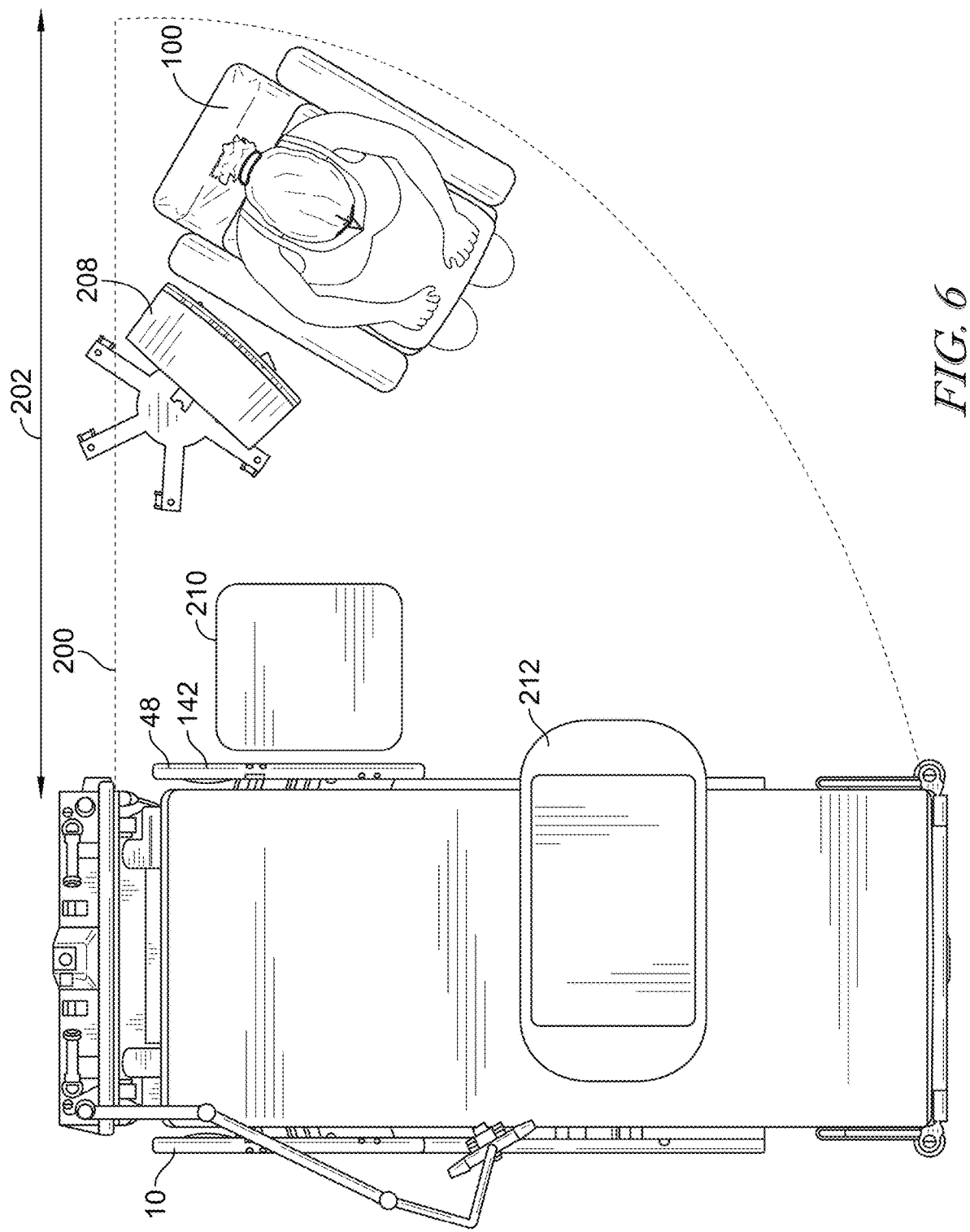
FIG. 6 is an overhead view of the field of view of the detector shown in FIG. 4.

Referring to FIG. 6, the field of view 200 extends for a range 202. In some embodiments, the range 202 is approximately 77 inches. In other embodiments, the range 202 may be within a range of 50 inches to 100 inches. The range 202 is configured to extend over the chair 100. A medical device 208, for example an electrocardiogram may be positioned between the bed 10 and the chair 100. The range 202 is configured to extend past such a medical device 208 to enable the detector 140 to detect the thermal radiation from the chair 100. However, the range 202 may be limited to prevent detecting thermal radiation from individuals or devices positioned beyond the chair 100. The detector 140 is positioned at the top 142 of the siderail 48 so that the field of view 200 extends over obstacles between the bed 10 and the chair 100. For example, a night stand 210 and a bed side table 212 are illustrated in FIG. 6. By positioning the detector 140 at the top 142 of the siderail 48, the field of view 200 extends over the night stand 210 and the bed side table 212.

Figure 7:
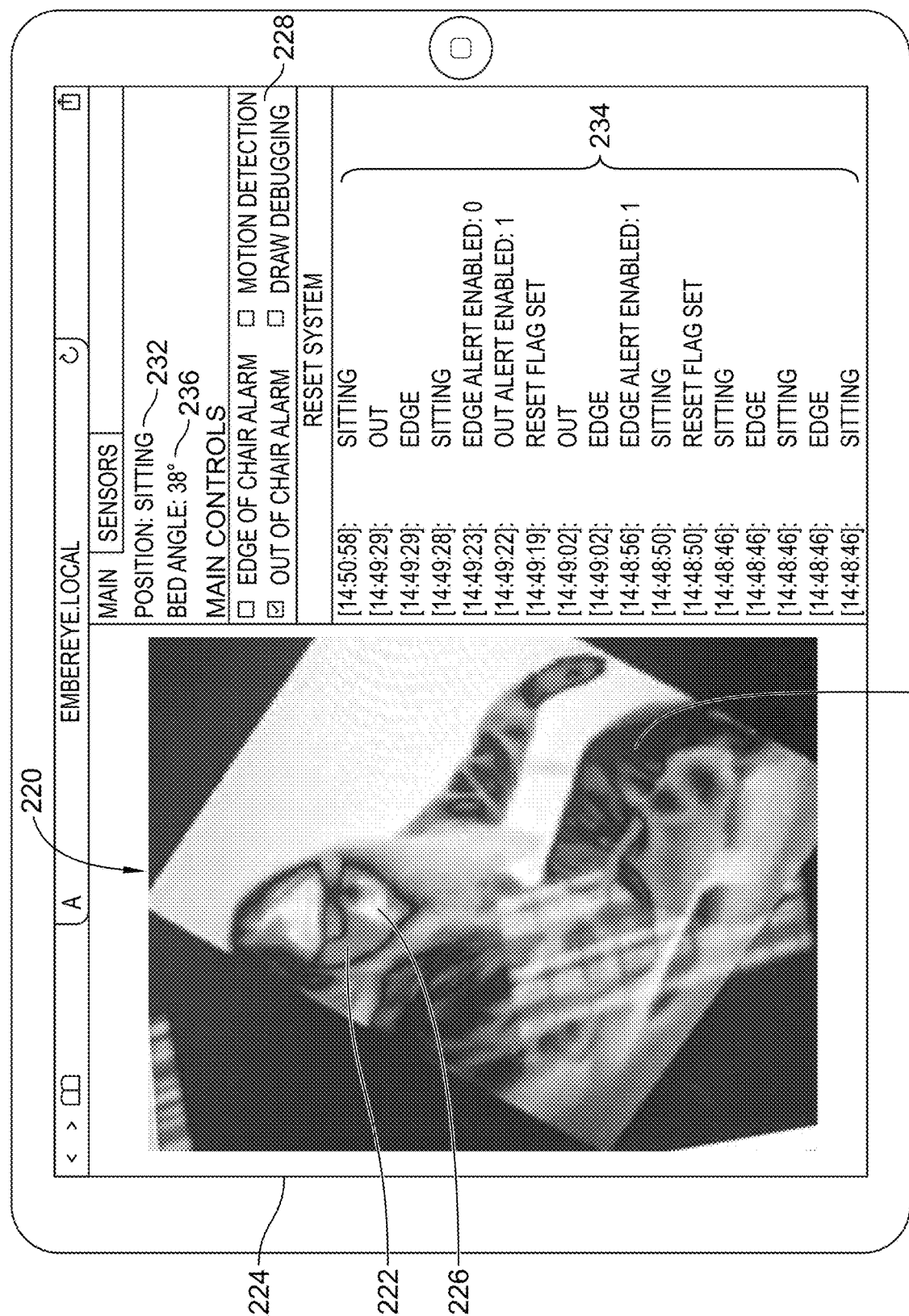
FIG. 7 is a plan view of a mobile device displaying a thermal image from the detector shown in FIG. 4.

Referring now to FIG. 7, the controller 160 generates a thermal image 220 from the thermal radiation detected by the detector 140. The thermal image 220 includes a thermal gradient that is indicative of various temperatures. As such, the detector 140 acquires thermal data that has a temperature value associated with each pixel in the thermal image 220. For example, higher detected temperatures 222 are displayed as a first colors, e.g. red. Lower detected temperatures 224 are displayed in a second color, e.g. blue. Intermediate temperatures 226 are displayed in at least one third color, e.g. yellow or orange. In some embodiments, the thermal image 220 may be displayed in greyscale with higher temperatures displayed in black and lower temperatures displayed in grey. In some embodiments, the higher temperatures may be displayed in a heavy cross-hatch and the lower temperatures may be displayed in a light cross-hatch.

The thermal image 220 is displayed on the remote devices 90. For example, the thermal image 220 may be displayed on a handheld device 230 carried by the caregiver, as shown in FIG. 7. The device 90 may also display additional information regarding the patient 310 and the bed 10. For example, in the illustrative embodiment, the device 90 displays the current position of the patient 310. As described in more detail below, the current position 232 may include sitting in the chair 100, exiting the chair 100, or out of the chair 100. Additionally, based on the settings of the PPM system 120, the device 90 may also indicate that the patient 310 is moving between the bed 10 and the chair 100. In one embodiment, the device 90 alerts the caregiver that the patient 310 is at risk of falling. A history 234 of the patient 310 movement is displayed on the device 90.

A bed angle 236 is also displayed on the device 90. By providing the bed angle 236, the caregiver may be alerted to assist the patient 310. For example, if the bed angle is 38 degrees, the patient 310 may have difficulty returning to the bed 10. Accordingly, if the caregiver is alerted at the device 90 that the patient 310 is moving from the chair 100 to the bed 10, the caregiver can enter the room to assist the patient 310 in lowering the bed 10 to an appropriate angle for entering the bed 10.

In some embodiments, the device 90 may also display the current temperature of the patient 310 based on the thermal image 220. As such, if the patient 310 is at risk of having a fever, the caregiver is alerted. Additionally, the thermal image 220 may assist the caregiver is detecting hot spots in the patient 310. For example, if an area of the patient's leg 238 is displayed as a higher detected temperature 222, the patient 310 may be at risk of developing ulcers or bed sores at that location. Accordingly, the caregiver is alerted to check that area of the patient 310 and to provide proper accommodations.

Figure 8:
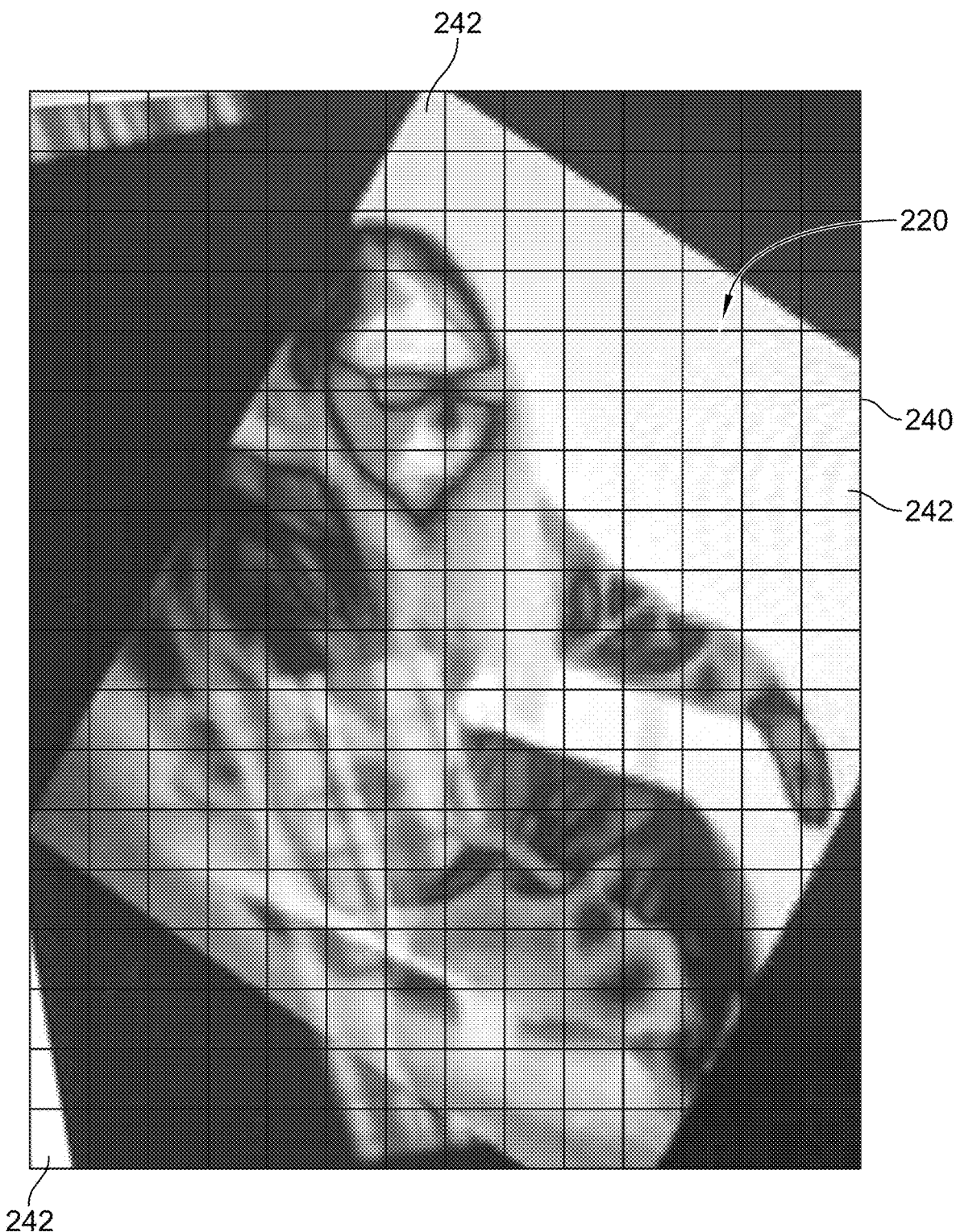
FIG. 8 is a plan view of the thermal image relative to a grid of the detector.

Mode selection inputs 228 are also provided on the device 90. In some embodiments, the mode selection inputs 228 may also be provided on the user inputs panel 130 as membrane switches or touch-screen switches and/or the GUI 88 as touch-screen switches. The mode selection inputs 228 enable the caregiver to arm a mode of the PPM system 120. The modes may include a Positioned in Chair Mode, a Chair Exit Mode, an Out of Chair Mode, a Movement Mode, or a Fall Detection Mode, as described above. In some embodiments, multiple modes may be armed simultaneously. In FIG. 8, the thermal image 220 is displayed over a grid 240 having a plurality of pixels 242. Each pixel's thermal data is filtered, selecting a range of the hottest pixels 242 within predetermined bounds for the hottest and coldest a human body should be. The controller 160 finds contours around the remaining unfiltered pixels 242. These contours represent each significant group of spatially close pixels 242. The contours are drawn onto the thermal image 220 as filled in closed shapes (in case the heat from the body is not uniform and there are gaps) and then are simplified using dilation and erosion techniques. The thermal image 220 is used to represent the "body" of the patient. "In chair" and "edge of chair" regions are selected based on the current bed angle measured by the controller 160. These regions are rectangular and can be different sizes and locations to best detect if the patient is in the chair, out of the chair or on the edge of the chair at a given bed angle.

Pixels 242 within the "in chair" region are counted and saved as the "initial body" pixel size. For the following frames from the thermal camera, body pixels 242 within the "in chair" and "edge of chair" regions are counted separately. If the number of body pixels 242 within the "in chair" region is less than 30% of the number of pixels 242 counted as the initial body, the out of chair alarm is triggered. If the number of body pixels 242 within the "edge of chair" region are greater than 50% of the initial body pixel count and the condition for an out of chair alarm is not satisfied, the edge of chair alarm is triggered. This alarm may be overridden by an out of chair alarm. If an out of chair alarm was previously triggered, the system can automatically reset and report that the patient is sitting in the chair if none of the conditions for an out of chair or edge of chair alarm are satisfied.

Accordingly, the controller 160 is configured to detect movement of a center of mass of the thermal image 220 relative to the grid 240. For example, if the center of mass of the thermal image 220 moves between pixels, such movement is indicative of movement of the patient 310. If the center of mass of the thermal image 220 moves within a first predetermined range of pixels 242, the controller 160 determines that the patient 310 is stationary or moving within the chair 100, but still positioned on the chair 100. If the center of mass of the thermal image 220 moves within a second predetermined range of pixels 242 that is greater than the first predetermined range, the controller 160 determines that the patient 310 is exiting the chair 100. If the center of mass of the thermal image 220 falls within a set of pixels 242 that do not include the chair 100, the controller 160 determines that the patient 310 has exited the chair 100. If the center of mass of the thermal image 220 moves within a third range of pixels 242 that is greater than the second range, the controller 160 determines that the patient 310 is moving between the bed 10 and the chair 100.

In some embodiments, movement of the center of mass of the thermal image 220 may also indicate a patient fall or a fall risk. The controller 160 is configured to detect an acceleration of the center of mass of the thermal image 220 in addition to the position of the center of mass of the thermal image 220 relative to the pixels 242. For example, a first set of the pixels 242 is indicative of the seat of the chair 100 and a second set of pixels 242 is indicative of the floor. If the center of mass of the thermal image 220 moves toward the second set of pixels 242, the controller determines that the patient 310 is moving toward the floor. If an acceleration of the center of mass of the thermal image 220 toward the floor exceeds a predetermined value, the controller 160 determines that the patient 310 is falling.

Figure 9:
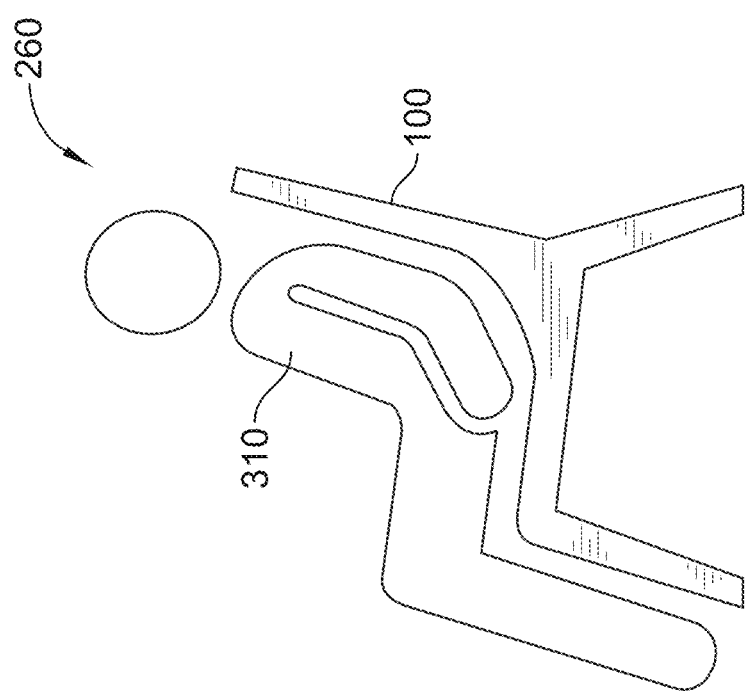
FIG. 9 is an elevation view of the patient positioned within the chair, wherein the PPM system is armed in a in Positioned in Chair Mode.

FIG. 9 illustrates the patient 310 positioned in the chair 100. The figure illustrated in FIG. 9 may represent an exemplary icon 260 that is displayed on the device 90, the user inputs panel 130, and/or the GUI 88, for arming the Positioned in Chair Mode of the PPM system 120. When the Positioned in Chair Mode is armed, the icon 260 appears on the device 90 and/or GUI 88. In some embodiments, the icon 260 is illuminated when the Positioned in Chair Mode is armed. In some embodiments, the icon 260 is displayed in a predetermined color when the Positioned in Chair Mode is armed. In other embodiments, other notifications, for example text, may be displayed on the device 90 or the GUI 88 to indicate that the Positioned in Chair Mode is armed. It will be appreciated that the Positioned in Chair Mode may be armed concurrently with any other mode described herein.

In the Positioned in Chair Mode, the PPM 120 monitors the position of the center of mass of the thermal image 220. The PPM system 120 monitors movement of the center of mass of the thermal image 220 relative to the pixels 242 to ensure that the center of mass of the thermal image 220 only moves within the first predetermined range of movement relative to the pixels 242. As long as the center of mass of the thermal image 220 is positioned within the first predetermined range of pixels 242, the PPM system 120 outputs data onto the device 90 and/or GUI 88 indicating that the patient 310 is positioned within the chair 100. While positioned in the chair, the PPM 120 may monitor the temperature of the patient 310 and alert the caregiver if the patient 310 is at risk of having a fever. The PPM system 120 may also monitor the temperature of the patient 310 and alert the caregiver of potential bed sores.

If the center of mass of the thermal image 220 is not detected by the PPM system 120 and/or if the center of mass of the thermal image 220 moves outside of the first predetermined range of pixels 242, the PPM system 120 alerts the caregiver that the patient 310 is no longer in the chair 100. By arming multiple modes of the PPM system 120, the caregiver may be alerted to other patient activities in addition to not be present in the chair 100. For example, the caregiver may be alerted that the patient 310 is no longer detected in the chair 100 and the patient 310 is exiting the chair 100 or the patient 310 has already exited the chair 100.

Figure 10:
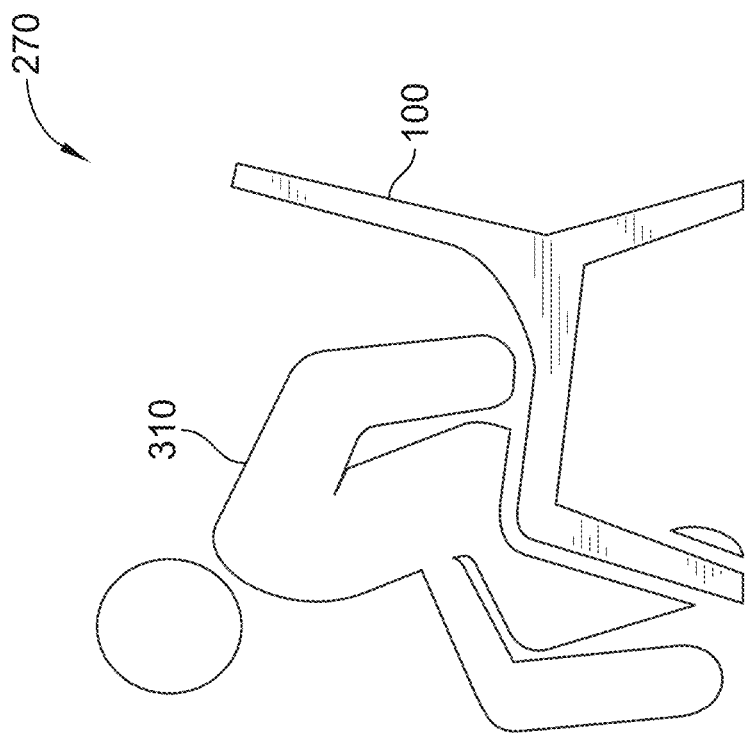
FIG. 10 is an elevation view of the patient exiting the chair, wherein the PPM system is armed in a Chair Exit Mode.

FIG. 10 illustrates the patient 310 exiting the chair 100. The figure illustrated in FIG. 10 may represent an exemplary icon 270 that is displayed on the device 90, the user inputs panel 130, and/or the GUI 88, for arming the Chair Exit Mode of the PPM system 120. When the Chair Exit Mode is armed, the icon 270 appears on the device 90 and/or GUI 88. In some embodiments, the icon 270 is illuminated when the Chair Exit Mode is armed. In some embodiments, the icon 270 is displayed in a predetermined color when the Chair Exit Mode is armed. In other embodiments, other notifications, for example text, may be displayed on the device 90 or the GUI 88 to indicate that the Chair Exit Mode is armed. It will be appreciated that the Chair Exit Mode may be armed concurrently with any other mode described herein.

In the Chair Exit Mode, the PPM 120 monitors the position of the center of mass of the thermal image 220. The PPM system 120 monitors movement of the center of mass of thermal image 220 relative to the pixels 242 to detect the center of mass of the thermal image 220 moving within the second predetermined range of movement relative to the pixels 242. When movement of the center of mass of the thermal image 220 occurs within the second predetermined range, the PPM system 120 determines that the patient 310 is in the process of exiting the chair 100. The PPM system 120 outputs data onto the device 90 and/or GUI 88 indicating that the patient 310 is exiting the chair 100.

At least one of the alerts 190 and/or 192 may be activated when the patient 310 is determined to be exiting the chair 100. The alerts 190, 192 are activated to communicate to the caregiver that the patient 310 may require assistance exiting the chair 100. In some embodiments, the alerts 190, 192 communicate directly to the patient 310. For example, an audible alert may direct the patient 310 to return to the chair 100. In addition to the activation of alerts 190, 192, an audible or visual alert may be activated at the bed 10 and/or the device 90. Accordingly, if the caregiver is not present in the room when the patient 310 begins exiting the chair 100, the alert on device 90 instructs the caregiver to return to the room to assist the patient 310.

The patient's chair exit activity is recorded in the history 234 with a time stamp. When the Chair Exit Mode is armed concurrently with the Positioned in Chair Mode, the history 234 will provide a complete synopsis of the patient activity, e.g. documentation of each time the patient 310 attempted to exit the chair 100 along with documentation of when the patient 310 returned to a position in the chair 100.

Figures 11, 12:
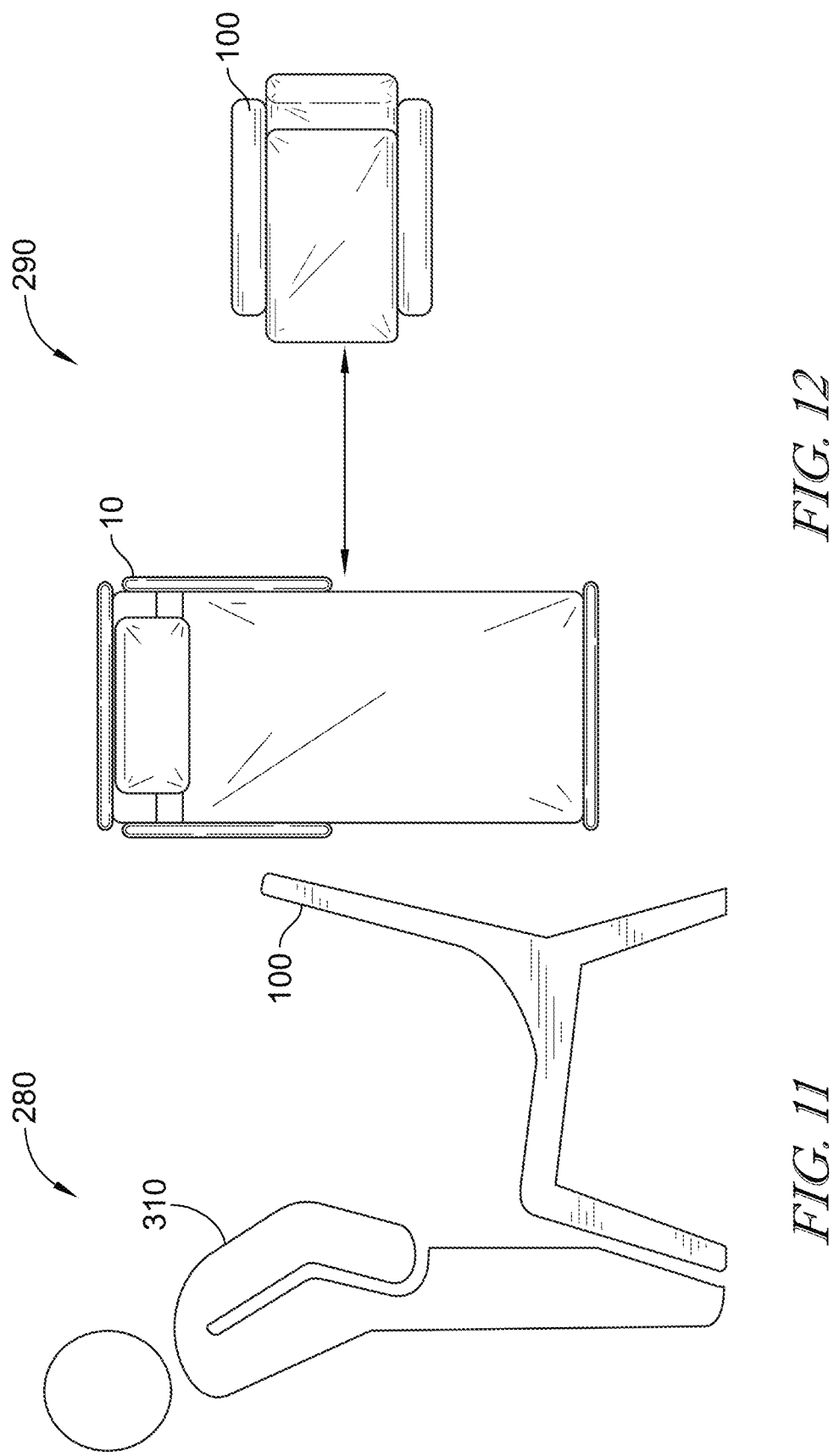
FIG. 11 is an elevation view of the patient out of the chair, wherein the PPM system is armed in an Out of Chair Mode.
FIG. 12 is an elevation view of the patient moving between the bed and the chair, wherein the PPM system is armed in a Movement Mode.

FIG. 11 illustrates the patient 310 out of the chair 100. The figure illustrated in FIG. 11 may represent an exemplary icon 280 that is displayed on the device 90, the user inputs panel 130, and/or the GUI 88, for arming the Out of Chair Mode of the PPM system 120. When the Out of Chair Mode is armed, the icon 280 appears on the device 90 and/or GUI 88. In some embodiments, the icon 280 is illuminated when the Out of Chair Mode is armed. In some embodiments, the icon 280 is displayed in a predetermined color when the Out of Chair Mode is armed. In other embodiments, other notifications, for example text, may be displayed on the device 90 or the GUI 88 to indicate that the Out of Chair Mode is armed. It will be appreciated that the Out of Chair Mode may be armed concurrently with any other mode described herein.

In the Out of Chair Mode, the PPM 120 monitors the position of the center of mass of the thermal image 220. The PPM system 120 monitors movement of the center of mass of the thermal image 220 relative to the pixels 242 to detect the center of mass of the thermal image 220 moving outside of a predetermined range of pixels 242 that includes the chair 100. When movement of the center of mass of the thermal image 220 occurs outside of the position of the chair, the PPM system 120 determines that the patient 310 has exited the chair 100. The PPM system 120 outputs data onto the device 90 and/or GUI 88 indicating that the patient 310 has exited the chair 100.

At least one of the alerts 190 and/or 192 may be activated when the patient 310 is determined to have exited the chair 100. The alerts 190, 192 are activated to communicate to the caregiver that the patient 310 may require assistance getting back in the chair 100, getting into the bed 10, or moving throughout the room, e.g. moving to the bathroom. In some embodiments, the alerts 190, 192 communicate directly to the patient 310. For example, an audible alert may direct the patient 310 to return to the chair 100. The alert 190, 192 may also direct the patient 310 to stay in position until help arrives. In addition to the activation of alerts 190, 192, an audible or visual alert may be activated at the bed 10 and/or the device 90. Accordingly, if the caregiver is not present in the room when the patient 310 has exited the chair 100, the alert on device 90 instructs the caregiver to return to the room to assist the patient 310.

The patient's chair exit activity is recorded in the history 234 with a time stamp. When the Out of Chair Mode is armed concurrently with the Positioned in Chair Mode, the history 234 will provide a complete synopsis of the patient activity, e.g. documentation of each time the patient 310 exited the chair 100 along with documentation of when the patient 310 returned to a position in the chair 100. By combining the Chair Exit Mode and the Out of Chair Mode, a history is provided of each time the patient 310 attempted to exit the chair 100 and each time the patient 310 successfully exited the chair 100.

FIG. 12 illustrates the patient 310 moving between the chair 100 and the bed 10. The figure illustrated in FIG. 12 may represent an exemplary icon 290 that is displayed on the device 90, the user inputs panel 130, and/or the GUI 88, for arming the Movement Mode of the PPM system 120. When the Movement Mode is armed, the icon 290 appears on the device 90 and/or GUI 88. In some embodiments, the icon 290 is illuminated when the Movement Mode is armed. In some embodiments, the icon 290 is displayed in a predetermined color when the Movement Mode is armed. In other embodiments, other notifications, for example text, may be displayed on the device 90 or the GUI 88 to indicate that the Movement Mode is armed. It will be appreciated that the Movement Mode may be armed concurrently with any other mode described herein.

In the Movement Mode, the PPM 120 monitors the position of the center of mass of the thermal image 220. The PPM system 120 monitors movement of the center of mass of the thermal image 220 relative to the pixels 242 to detect the center of mass of the thermal image 220 moving within the third predetermined range of pixels 242 between the chair 100 and the bed 10. When movement of the center of mass of the thermal image 220 occurs within the third predetermined range of pixels 242, the PPM system 120 determines that the patient 310 is moving between the bed 10 and the chair 100. The PPM system 120 outputs data onto the device 90 and/or GUI 88 indicating that the patient 310 is moving between the bed 10 and the chair 100. In some embodiments, the Movement Mode is armed when the patient 310 is positioned in the chair 100 to detect movement from the chair 100 to the bed 10. In other embodiments, the Movement Mode is armed when the patient 310 is in the bed 10 to detect movement of the patient 310 from the bed 10 to the chair 100. In such an embodiment, the detected movement to the chair 100 alerts the caregiver to arm one of the other modes, for example Positioned in Chair Mode, Chair Exit Mode, Out of Chair Mode, and/or Fall Detection Mode. In some embodiments, the detected movement to the chair 100 automatically arms one of the other modes, for example Positioned in Chair Mode, Chair Exit Mode, Out of Chair Mode, and/or Fall Detection Mode.

At least one of the alerts 190 and/or 192 may be activated when the patient 310 is determined to be moving between the chair 100 and the bed 10. The alerts 190, 192 are activated to communicate to the caregiver that the patient 310 may require assistance getting into the chair 100 or getting into the bed 10. In some embodiments, the alerts 190, 192 communicate directly to the patient 310. For example, an audible alert may direct the patient 310 to return to the chair 100 or the bed 10. The alert 190, 192 may also direct the patient 310 to stay in position until help arrives. In addition to the activation of alerts 190, 192, an audible or visual alert may be activated at the bed 10 and/or the device 90. Accordingly, is the caregiver is not present in the room when the patient 310 is moving, the alert on device 90 instructs the caregiver to return to the room to assist the patient 310.

The patient's chair exit activity is recorded in the history 234 with a time stamp. When the Movement Mode is armed, the history 234 provides a complete synopsis of the patient activity, e.g. documentation of each time the patient 310 moved from the Chair 100 to the bed 10.

Figure 13:
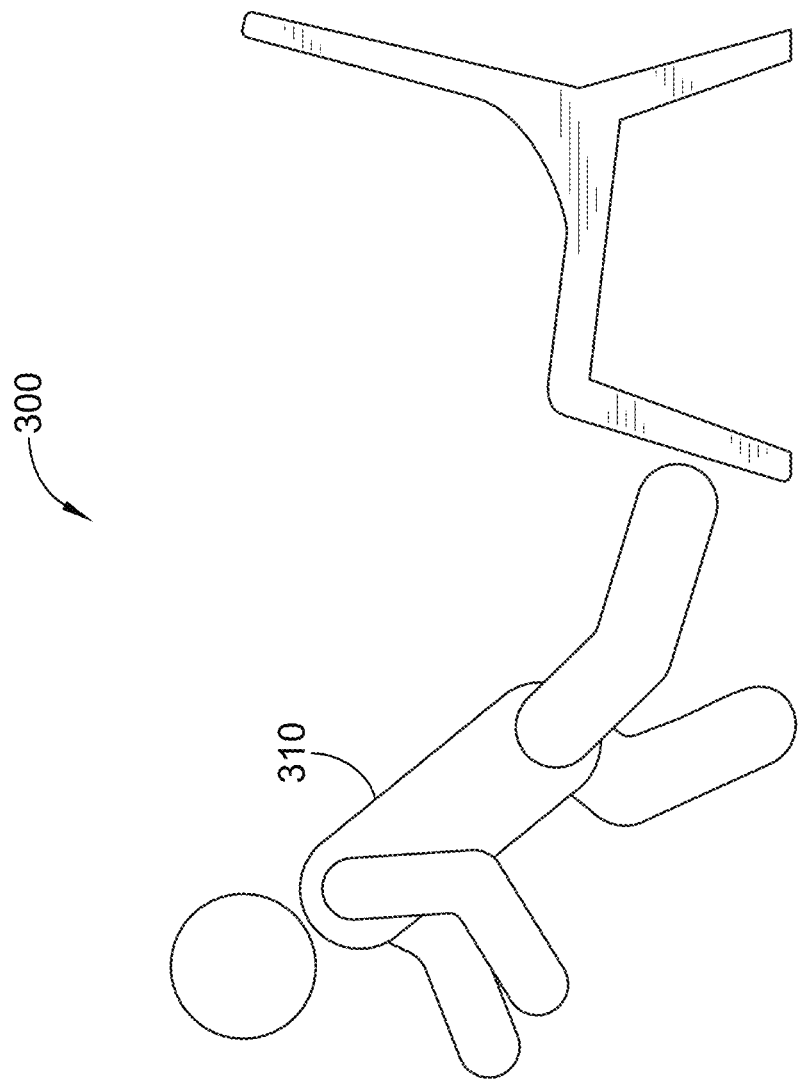
FIG. 13 is an elevation view of the patient having a fall event, wherein the PPM system is armed in a Fall Detection Mode

FIG. 13 illustrates the patient 310 experiencing a fall event. The figure illustrated in FIG. 13 may represent an exemplary icon 300 that is displayed on the device 90, the user inputs panel 130, and/or the GUI 88, for arming the Fall Detection Mode of the PPM system 120. When the Fall Detection Mode is armed, the icon 300 appears on the device 90 and/or GUI 88. In some embodiments, the icon 300 is illuminated when the Fall Detection Mode is armed. In some embodiments, the icon 300 is displayed in a predetermined color when the Fall Detection Mode is armed. In other embodiments, other notifications, for example text, may be displayed on the device 90 or the GUI 88 to indicate that the Fall Detection Mode is armed. It will be appreciated that the Fall Detection Mode may be armed concurrently with any other mode described herein.

In the Fall Detection Mode, the PPM 120 monitors the position and acceleration of the center of mass of the thermal image 220. The PPM system 120 monitors movement and acceleration of the center of mass of the thermal image 220 relative to the pixels 242 to detect the thermal image 220 moving toward the floor at a predetermined rate of speed. When the predetermined movement of the center of mass of the thermal image 220 occurs, the PPM system 120 determines that the patient 310 is at risk of falling. The PPM system 120 outputs data onto the device 90 and/or GUI 88 indicating that the patient 310 is at risk of falling.

At least one of the alerts 190 and/or 192 may be activated when the patient 310 is determined to be at risk of falling. The alerts 190, 192 are activated to communicate to the caregiver that the patient 310 may require assistance getting into the chair 100 or getting into the bed 10. In some embodiments, the alerts 190, 192 communicate directly to the patient 310. For example, an audible alert may direct the patient 310 to return to the chair 100 or the bed 10. The alert 190, 192 may also direct the patient 310 to stay in position until help arrives. In addition to the activation of alerts 190, 192, an audible or visual alert may be activated at the bed 10 and/or the device 90. Accordingly, is the caregiver is not present in the room when the patient 310 is falling, the alert on device 90 instructs the caregiver to return to the room to assist the patient 310.

The patient's chair exit activity is recorded in the history 234 with a time stamp. When the Fall Detection Mode is armed, the history 234 provides a complete synopsis of the patient activity, e.g. documentation of each time a fall event occurred.

The embodiments described herein utilize a thermal camera to monitor patient movement, so there is no need for pads on the patient chair. Using the described embodiments, patient chairs are upgraded to smart chairs. The first three modes include Position, Exiting, and Out of Bed. In addition, a fourth mode detecting movement between the bed and chair allows the patient to move between the bed and chair while rearming automatically within a set amount of time. A fifth mode is utilized to detect patient falls. Electronics are located in the left and right head rails monitoring the left and right sides of the bed. In some embodiments, one set of electronics utilizing an intravenous pole monitors the whole bed.

The sensor may be a FLIR camera with a viewing angle of approximately a 65-degree cone scanning field. Coupled with an accelerometer, the FLIR camera can monitor the patient chair from 0 degrees to 65 degrees of articulation. The FLIR camera is mounted in the line manager of the blow-molded side rail. The system is wirelessly controlled with any smart device. The system may also include a stereo camera or lidar.

The system provides the mode sensing without the use of a pad. In addition, the modes can be coupled together to create additional functionality. Also, leveraging the current systems, the chair sensor can utilize vocal warnings as well as illuminations. Because the sensor is a FLIR, it can monitor patient temperature. The system could also alert caregivers if the system detects that a patient temperature spike or a localized hotspot indicative of a pressure injury.

The system may reduce patient falls, leverage current bed exit connectivity already equipped on the bed, and reduce nurse workload when equipped on smart devices. The system provides potential savings for the health care facility because the caregiver can view the patient in isolation without going into the room.

The system enables coupling the Exit Mode with a voice prompt reminding patient to sit back into chair before alerting. The system also enables coupling the Exit Mode with the Out of Chair Mode. The system may reduce the need for camera surveillance and patient advocates. The system also allows the patient to move between bed and chair with more freedom while still allow for monitoring. The system provides an alternative for fall risk patients that are more comfortable in the patient chair and promotes early mobility protocols.

All of the modes combine audible beeps (in room), voice prompts (in room), and sending messages to connected nursing communication devices when alerting. The modes are not limited to the modes described above and may include combination modes. A Position mode monitors the patient and alerts for slight movement. The Position mode is the most sensitive. An Exiting mode monitors the patient movement in the chair. The Exiting mode sends alerts when the patient is at the edge of the chair. The Out of Chair mode sends alerts when the patient has left the chair. An Up Ad Lib mode monitors movement from the bed to the chair and allows the patient to leave bed and get into the patient chair. Once the patient is in the chair, the Chair Alert Mode sets to whatever mode the caregiver has preset system to. Another Up Ad Lib monitors movement from the chair to the bed and allows the patient to leave the chair and get into the bed. A Bed Exit sets to whatever bed mode the caregiver has preset system to. A first Combo Mode includes Position mode and Exiting mode. When patient movement is detected, a voice prompt reminds the patient to stay still and remain seated. This mode sends alerts when patient is at the edge of the chair. A second Combo Mode includes Exiting mode and Out of Chair mode. When the patient moves to the edge of the chair, a voice prompt reminds the patient to remain in the chair. This mode sends alerts when the patient leaves the chair.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used, the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles have been presented, they need not be utilized in combination, and many combinations of aspects and principles are possible in light of the various embodiments provided above.

The invention claimed is:

1. A system for contactless monitoring of a person in a chair, the system comprising:
    a detector mount positioned adjacent the chair and detached from the chair, wherein the detector mount is formed in a siderail of a bed positioned adjacent the chair,
    a detector positioned in the detector mount and configured to detect thermal radiation from a field of view that includes the chair, and
    a controller configured to control the detector, the controller including a processor and a nontransitory memory device that includes instructions that are performed by the processor to control the detector,
    wherein the controller is configured to process data related to the thermal radiation from the field of view and detected by the detector to determine a status of the person from one of at least three statuses.

2. The system of claim 1, wherein the one of at least three statuses includes positioned in the chair, in the process of exiting the chair, and out of the chair.

3. The system of claim 2, further comprising an alert system configured to alert the person to return to the position in the chair when the person is determined to be exiting the chair.

4. The system of claim 1, wherein the controller is further configured to determine a fourth status of the person by processing the data related to the thermal radiation from the field of view, wherein the fourth status is that the person is moving between the chair and a patient support apparatus.

5. The system of claim 4, wherein the controller is further configured to determine a fifth status of the person by processing the data related to the thermal radiation from the field of view, wherein the fifth status includes determining that the person is falling based on a rate of change in the thermal radiation in the field of view.

6. The system of claim 1, wherein the field of view includes a 65 degree cone scanning field that is broad enough to view the chair.

7. The system of claim 1, wherein the controller is further configured to determine a temperature of the person by processing the data related to the thermal radiation from the field of view.

8. The system of claim 7, wherein the controller is further configured to alert a caregiver if the temperature of the person exceeds a predetermined value.

9. The system of claim 7, wherein the controller identifies pressure sores on the person based on the detected temperature of the person.

10. The system of claim 1, wherein the detector includes a thermal camera.

11. The system of claim 1, further comprising a remote display device to display a thermal image from the field of view.

12. A system for contactless monitoring of a person, the system comprising:
 a first patient support apparatus,
 a second patient support apparatus positioned adjacent to and detached from the first patient support apparatus,
 a detector coupled to the first patient support apparatus and configured to detect thermal radiation from a field of view detected by the detector and including the second patient support apparatus, and
 a controller configured to control the detector, the controller including a processor and a nontransitory memory device that includes instructions that are performed by the processor to control the detector,
 wherein the controller is incorporated into the first patient support apparatus and in communication with a control system of the first patient support apparatus,
 wherein the controller is configured to process data related to the thermal radiation from the field of view to determine a status of a person at the second patient support apparatus from one of at least three statuses.

13. The system of claim 12, wherein the first patient support apparatus includes a bed and the second patient support apparatus includes a chair.

14. The system of claim 12, wherein the detector positioned in a siderail of the first patient support apparatus.

15. The system of claim 12, wherein the detector is coupled to an intravenous pole of the first patient support apparatus.

16. The system of claim 12, wherein the one of at least three statuses includes positioned in the second patient support apparatus, in the process of exiting the second patient support apparatus, and out of the second patient support apparatus.

17. The system of claim 12, wherein the controller is further configured to determine a fourth status of the person by processing the data related to the thermal radiation from the field of view, wherein the fourth status is that the person is moving between the second patient support apparatus and the first patient support apparatus.

18. The system of claim 17, wherein the controller is further configured to determine a fifth status of the person by processing the data related to the thermal radiation from the field of view, wherein the fifth status includes determining that the person is falling based on a rate of change in the thermal radiation in the field of view.

19. The system of claim 12, wherein the field of view includes a 65 degree cone scanning field that is broad enough to view the second patient support apparatus.

20. The system of claim 12, wherein the controller is further configured to determine a temperature of the person by processing the data related to the thermal radiation from the field of view.

* * * * *